(12) United States Patent
Garde

(10) Patent No.: US 9,095,282 B2
(45) Date of Patent: Aug. 4, 2015

(54) SYSTEM AND METHOD FOR TREATING DYSPHAGIA

(75) Inventor: Smita Garde, Irvine, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 504 days.

(21) Appl. No.: 13/502,418

(22) PCT Filed: Oct. 11, 2010

(86) PCT No.: PCT/IB2010/054598
§ 371 (c)(1),
(2), (4) Date: Apr. 17, 2012

(87) PCT Pub. No.: WO2011/048524
PCT Pub. Date: Apr. 28, 2011

(65) Prior Publication Data
US 2012/0209089 A1    Aug. 16, 2012

Related U.S. Application Data

(60) Provisional application No. 61/253,862, filed on Oct. 22, 2009.

(51) Int. Cl.
*A61B 5/00*  (2006.01)
*A61B 5/103*  (2006.01)
(Continued)

(52) U.S. Cl.
CPC ............... *A61B 5/103* (2013.01); *A61B 5/4205* (2013.01); *A61M 16/00* (2013.01); *A61M 16/0051* (2013.01); *A61M 16/161* (2014.02); *G06F 19/3406* (2013.01); *G06F 19/3481* (2013.01);
(Continued)

(58) Field of Classification Search
CPC ..... A61B 5/4205; A61B 5/087; A61B 5/4833
USPC .......................................... 600/301, 593, 595
See application file for complete search history.

(56) References Cited

U.S. PATENT DOCUMENTS

| | | | | |
|---|---|---|---|---|
| 5,980,498 A * | 11/1999 | Brown et al. | ................ | 604/327 |
| 6,105,575 A | 8/2000 | Estes | | |
| 6,652,481 B1 * | 11/2003 | Brown et al. | .................. | 604/35 |
| 7,749,177 B2 * | 7/2010 | Chau et al. | ................... | 600/593 |
| 8,388,561 B2 * | 3/2013 | Ludlow et al. | ................. | 601/48 |

(Continued)

FOREIGN PATENT DOCUMENTS

| WO | 2006116843 A1 | 11/2006 |
|---|---|---|
| WO | WO 2006116843 A1 * | 11/2006 |
| WO | WO 2011107860 A1 * | 9/2011 |

OTHER PUBLICATIONS

Martin-Harris, Bonnie "Coordination of Respiration and Swallowing" Gimotility Online, May 16, 2006, pp. 1-29 and 1-5, Naure Publishing Group.

*Primary Examiner* — Sean Dougherty
(74) *Attorney, Agent, or Firm* — Randall M. Berman

(57) ABSTRACT

Dysphagia of a subject (12) is treated. The treatment of dysphagia may include providing cues to the subject (12) that prompt the subject to swallow, and monitoring the response of the subject (12) to the cues. The swallowing function of the subject (12) may be analyzed over a single therapy session and/or over time to evaluate the general progress of the subject (12). A pressurized flow of breathable gas may be provided to the airway of the subject (12) during the therapy. The pressurized flow of breathable gas may remove certain discomfort associated with the dysphagia of the subject (12), such as shortness of breath, and also provides a therapy to improve the coordination of breathing and swallowing in the subject (12).

11 Claims, 3 Drawing Sheets

(51) Int. Cl.
  *A61M 16/00* (2006.01)
  *G06F 19/00* (2011.01)
  *A61M 16/16* (2006.01)
  *A61M 16/10* (2006.01)

(52) U.S. Cl.
  CPC .......... *A61M 2016/0027* (2013.01); *A61M 2016/0033* (2013.01); *A61M 2016/102* (2013.01); *A61M 2205/3365* (2013.01); *A61M 2205/3368* (2013.01); *A61M 2205/3375* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2230/005* (2013.01); *A61M 2230/60* (2013.01)

(56) References Cited

U.S. PATENT DOCUMENTS

| | | | |
|---|---|---|---|
| 8,540,660 B2 * | 9/2013 | Martin et al. | 604/24 |
| 8,579,839 B2 * | 11/2013 | Ludlow et al. | 601/46 |
| 8,652,040 B2 * | 2/2014 | LeBoeuf et al. | 600/301 |
| 2004/0249264 A1 | 12/2004 | Salgo | |
| 2005/0263152 A1 * | 12/2005 | Fong | 128/200.24 |
| 2005/0283096 A1 * | 12/2005 | Chau et al. | 600/593 |
| 2006/0210480 A1 * | 9/2006 | Hamdy | 424/10.1 |
| 2006/0282010 A1 * | 12/2006 | Martin et al. | 600/560 |
| 2008/0269646 A1 * | 10/2008 | Chau et al. | 600/595 |
| 2009/0187124 A1 * | 7/2009 | Ludlow et al. | 601/47 |
| 2009/0227908 A1 * | 9/2009 | Chau et al. | 600/595 |
| 2010/0049103 A1 * | 2/2010 | Ludlow et al. | 601/46 |

* cited by examiner

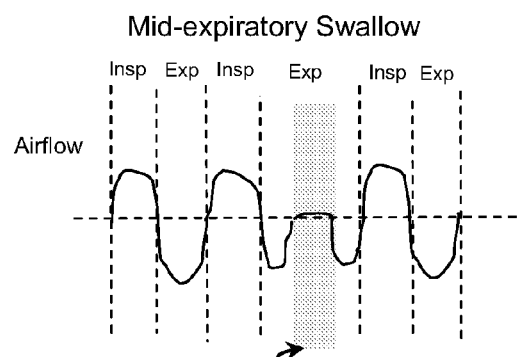
FIG. 2 Mid-expiratory Swallow
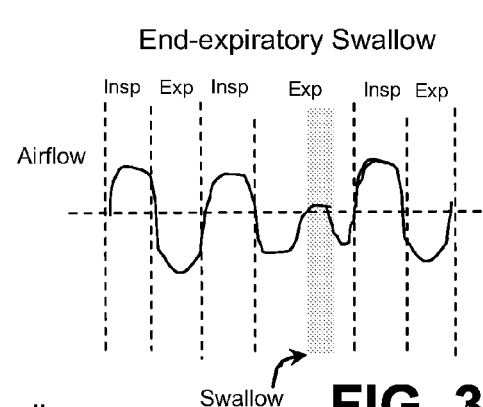
FIG. 3 End-expiratory Swallow
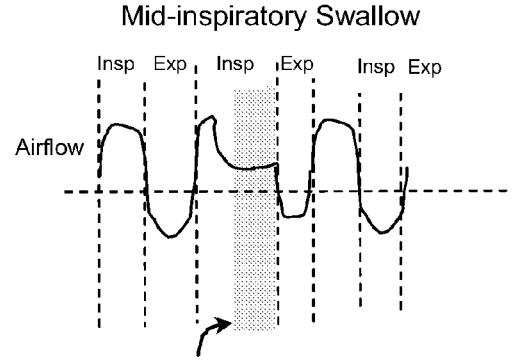
FIG. 4 Mid-inspiratory Swallow

SYSTEM AND METHOD FOR TREATING DYSPHAGIA

BACKGROUND OF THE INVENTION

1. Field of the Invention

The invention relates to the treatment of dysphagia by prompting a subject to swallow at a point in time that is coordinated with breathing cycle, and then monitoring the response of the subject to swallowing.

2. Description of the Related Art

Dysphagia is swallowing dysfunction. Dysphagia is commonly present in subjects with neurological, structural, and/or cognitive disorders. The impact to quality of life for dysphagia patients may be substantial. For example, subjects suffering from dysphagia may be affected by chronic malnutrition, dehydration, failure to thrive, aspiration pneumonia, and exacerbation of chronic lung disease.

Generally, conventional therapies for dysphagia include dietary modification, compensatory techniques like postural alterations, indirect therapy like strengthening exercises for swallowing muscles, and direct therapy like exercises during swallowing.

SUMMARY OF THE INVENTION

One aspect of the invention relates to a system configured to treat dysphagia of a subject. In one embodiment, the system comprises a user interface, a sensor, and a processor. The user interface is configured to convey information to a subject. The sensor is configured to generate an output signal indicating the status of swallowing. The processor is configured to execute computer program modules. The computer program modules comprise a swallowing cue module and a swallowing module. The swallowing cue module is configured to control the user interface to provide swallowing cues to the subject that indicate the subject should attempt to swallow. The swallowing module is configured to determine a response of the subject to a swallowing cue provided to the subject by the user interface, wherein the swallowing module determines the response of the subject based on the output signal of the sensor.

Another aspect of the invention relates to a method of treating dysphagia of a subject. In one embodiment, the method comprises generating an output signal indicating whether or not the subject is swallowing; providing a swallowing cue to the subject that indicates the subject should attempt to swallow; and determining a response of the subject to the swallowing cue provided to the subject based on the output signal of the sensor.

Yet another aspect of the invention relates to a system configured to treat dysphagia of a subject. In one embodiment, the system comprises means for generating an output signal indicating whether or not the subject is swallowing; means for providing a swallowing cue to the subject that indicates the subject should attempt to swallow; and means for determining a response of the subject to the swallowing cue provided to the subject based on the output signal of the sensor.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 2 illustrates a plot of airflow at the airway of a subject versus time, as the subject swallows.

FIG. 3 illustrates a plot of airflow at the airway of a subject versus time, as the subject swallows.

FIG. 4 illustrates a plot of airflow at the airway of a subject versus time, as the subject swallows.

DETAILED DESCRIPTION OF THE EXEMPLARY EMBODIMENTS

Figure 1:
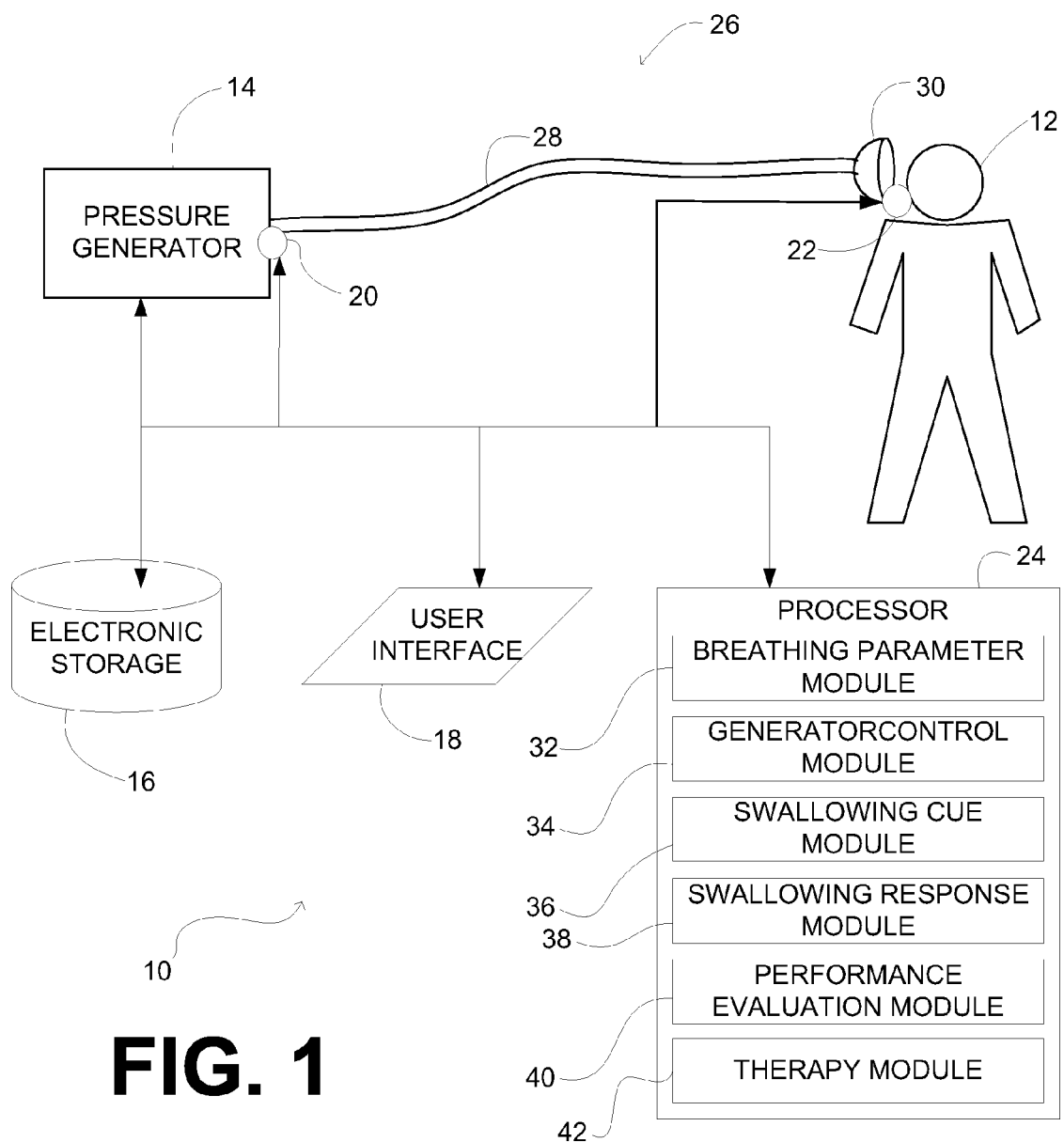
FIG. 1 illustrates a system configured to treat dysphagia of a subject, in accordance with one or more embodiments of the invention.

FIG. 1 illustrates a system 10 configured to treat dysphagia of a subject 12. The treatment of dysphagia may include providing cues to subject 12 that prompt subject 12 to swallow, and monitoring the response of subject 12 to the cues. The swallowing function of subject 12 may be analyzed over a single therapy session and/or over time to evaluate the general progress of subject 12. The system 10 may provide a pressurized flow of breathable gas to the airway of subject 12 during the therapy. The pressurized flow of breathable gas may remove certain discomfort associated with the dysphagia of subject 12, such as shortness of breath caused by swallowing. In one embodiment, system 10 includes one or more of a pressure generator 14, electronic storage 16, a user interface 18, one or more gas parameter sensors 20, one or more swallowing sensors 22, a processor 24, and/or other components.

In one embodiment, pressure generator 14 is configured to generate a pressurized flow of breathable gas for delivery to the airway of subject 12. The pressure generator 14 may control one or more parameters of the pressurized flow of breathable gas (e.g., flow rate, pressure, volume, humidity, temperature, gas composition, etc.) for therapeutic purposes, or for other purposes. By way of non-limiting example, pressure generator 14 may be configured to control the pressure of the pressurized flow of breathable gas to provide pressure support to the airway of subject 12. The pressure generator 14 may include a positive pressure generator such as, for example, the device described in U.S. Pat. No. 6,105,575, hereby incorporated by reference in its entirety.

The pressurized flow of breathable gas is delivered to the airway of subject 12 via a subject interface 26. Subject interface 26 is configured to communicate the pressurized flow of breathable gas generated by pressure generator 14 to the airway of subject 12. As such, subject interface 26 includes a conduit 28 and an interface appliance 30. Conduit conveys the pressurized flow of breathable gas to interface appliance 30, and interface appliance 30 delivers the pressurized flow of breathable gas to the airway of subject 12. Some examples of interface appliance 30 may include, for example, a nasal cannula, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., generator 14, user interface 18, processor 24, etc.).

User interface 18 is configured to provide an interface between system 10 and subject 12 through which subject 12 may provide information to and receive information from system 10. This enables data, cues, results, and/or instructions and any other communicable items, collectively referred to as "information," to be communicated between the subject 12 and one or more of generator 14, electronic storage 16, and/or processor 24. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

The gas parameter sensors 20 are configured to generate one or more output signals conveying information related to one or more parameters of the pressurized flow of breathable gas. The one or more parameters may include, for example, one or more of a flow rate, a volume, a pressure, a composition (e.g., concentration(s) of one or more constituents), humidity, temperature, acceleration, velocity, acoustics, changes in a parameter indicative of respiration, and/or other gas parameters. The gas parameter sensors 20 may include one or more sensors that measure such parameters directly (e.g., through fluid communication with the pressurized flow of breathable gas at pressure generator 14 or in subject interface 26). The gas parameter sensors 20 may include one or more sensors that generate output signals related to one or more parameters of the pressurized flow of breathable gas indirectly. For example, one or more of gas parameter sensors 20 may generate an output based on an operating parameter of pressure generator 14 (e.g., a valve driver or motor current, voltage, rotational velocity, and/or other operating parameters), and/or other sensors. Although gas parameter sensors 20 are illustrated at a single location at or adjacent to pressure generator 14, this is not intended to be limiting. The gas parameter sensors 20 may include sensors disposed in a plurality of locations, such as for example, within pressure generator 14, within (or in communication with) conduit 28, within (or in communication with) interface appliance 30, and/or other locations.

The swallowing sensors 22 are configured to generate one or more output signals indicating status of swallowing by subject 12. The status of swallowing may include whether or not subject 12 is swallowing, and/or other statuses. By way of non-limiting example, swallowing sensors 22 may include one or more electromyographic sensors installed on or near the neck of subject 12, one or more microphones installed on or near the neck of subject 12, one or more vibration detectors installed on or near the neck of subject 12, and/or other sensors. Although swallowing sensors 22 are illustrated in FIG. 1 as being separate from gas parameter sensors 20, in one embodiment, some or all of swallowing sensors 22 are included in gas parameter sensors 20. Since swallowing causes subject 12 to momentarily pause respiration, the output signals generated by gas parameter sensors 20 may provide an indication as to whether subject 12 is swallowing (e.g., has momentarily paused respiration).

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination.

As is shown in FIG. 1, processor 24 may be configured to execute one or more computer program modules. The one or more computer program modules may include one or more of a breathing parameter module 32, a generator control module 34, a swallowing cue module 36, a swallowing response module 38, a performance evaluation module 40, a therapy module 42, and/or other modules. Processor 24 may be configured to execute modules 32, 34, 36, 38, 40, and/or 42 by software; hardware; firmware; some combination of software, hardware, and/or firmware; and/or other mechanisms for configuring processing capabilities on processor 24.

It should be appreciated that although modules 32, 34, 36, 38, 40, and 42 are illustrated in FIG. 1 as being co-located within a single processing unit, in implementations in which processor 24 includes multiple processing units, one or more of modules 32, 34, 36, 38, 40, and/or 42 may be located remotely from the other modules. The description of the functionality provided by the different modules 32, 34, 36, 38, 40, and/or 42 described below is for illustrative purposes, and is not intended to be limiting, as any of modules 32, 34, 36, 38, 40, and/or 42 may provide more or less functionality than is described. For example, one or more of modules 32, 34, 36, 38, 40, and/or 42 may be eliminated, and some or all of its functionality may be provided by other ones of modules 32, 34, 36, 38, 40, and/or 42. As another example, processor 24 may be configured to execute one or more additional modules that may perform some or all of the functionality attributed below to one of modules 32, 34, 36, 38, 40, and/or 42.

The breathing parameter module 32 is configured to determine one or breathing parameters of the respiration of subject 12. The breathing parameter module 32 determines the one or more breathing parameters of the respiration of subject 12 based on the output signals generated by gas parameter sensors 20. The one or more breathing parameters determined by breathing parameter module 32 may include one or more of tidal volume, peak flow, respiration rate, timing of breathing transitions (e.g., from inhalation to exhalation, from exhalation to inhalation, and/or other transitions), flow contour, flow limitation, and/or other breathing parameters.

The generator control module 34 is configured to control pressure generator 14 to adjust the parameters of the pressurized flow of breathable gas in accordance with a therapy mode. A non-limiting example of one such mode is Continuous Positive Airway Pressure (CPAP). CPAP has been used for many years and has proven to be helpful in promoting regular breathing. Another mode for generating the pressurized flow of breathable gas is bi-level positive air pressure mode (BIPAP®). In bi-level positive air pressure mode, two levels of positive air pressure (HI and LO) are supplied to a patient. Other modes of generating the pressurized flow of breathable gas are contemplated. Generally, the timing of the HI and LO levels of pressure are controlled such that the HI level of positive air pressure is delivered to subject 12 during inhalation (known as Inspiratory Positive Airway Pressure or IPAP) and the LO level of pressure is delivered to subject 12 during exhalation (known as Expiratory Positive Airway Pressure or EPAP). The timing of adjustments to the parameters of the pressurized flow of breathable gas in accordance with a therapy mode may be determined by generator control module 34 based on the one or more breathing parameters determined by breathing parameter module 32.

It will be appreciated that in one or more embodiments the therapy of subject 12 for dysphagia may be executed without the delivery of a pressurized flow of breathable gas to the airway of subject 12 (e.g., without pressure generator 14 and/or generator control module 34). However, the delivery of the pressurized flow of breathable gas may facilitate respiration by subject 12 during the therapy. Since shortness of breath caused by swallowing is common in subjects suffering from dysphagia, the delivery of the pressurized flow of breathable gas may make swallowing more comfortable to subject 12, and may enable subject 12 to concentrate on aspects of swallowing other than breathing (e.g., muscle control, coordination, etc.). The delivery of the pressurized flow of breathable gas may lengthen expiration, which may further facilitate proper swallowing by subject 12 (e.g., as discussed below).

The swallowing cue module 36 is configured to control the generation of swallowing cues to be provided to subject 12 indicating subject 12 should attempt to swallow. The breathing cues may be generated by user interface 18 under the control of swallowing cue module 36. In controlling the generation of a swallowing, swallowing cue module 36 determines a point in time at which the swallowing cue should be generated, and initiates generation of the swallowing cue at the determined point in time. The swallowing cue module 36 determines the point in time at which the swallowing cue should be generated based on the one or more breathing parameters determined by breathing parameter module 32 and/or swallowing parameters determined by swallowing response module 38.

Subjects with dysphagia are often unable to properly coordinate the timing of swallows with respiration, which may result in shortness of breath, aspiration, coughing, choking, and/or other effects. By way of illustration, FIGS. 2-4 illustrate plots of airflow versus time showing the impact of swallowing on the respiration of a normal subject (e.g., a subject not suffering from dysphagia). Specifically, FIG. 2 shows how a normal subject who swallows during expiration pauses the expiration to swallow, and then resumes expiration before inspiration begins. FIG. 3 shows how, in normal subjects, swallows that occur in late expiration are shorter than those that occur earlier in expiration (e.g., as shown in FIG. 2), and are still followed by a short resumption of expiration before inspiration begins. FIG. 4 shows how for a normal subject a swallow during inspiration resets the respiratory cycle.

Figure 5:
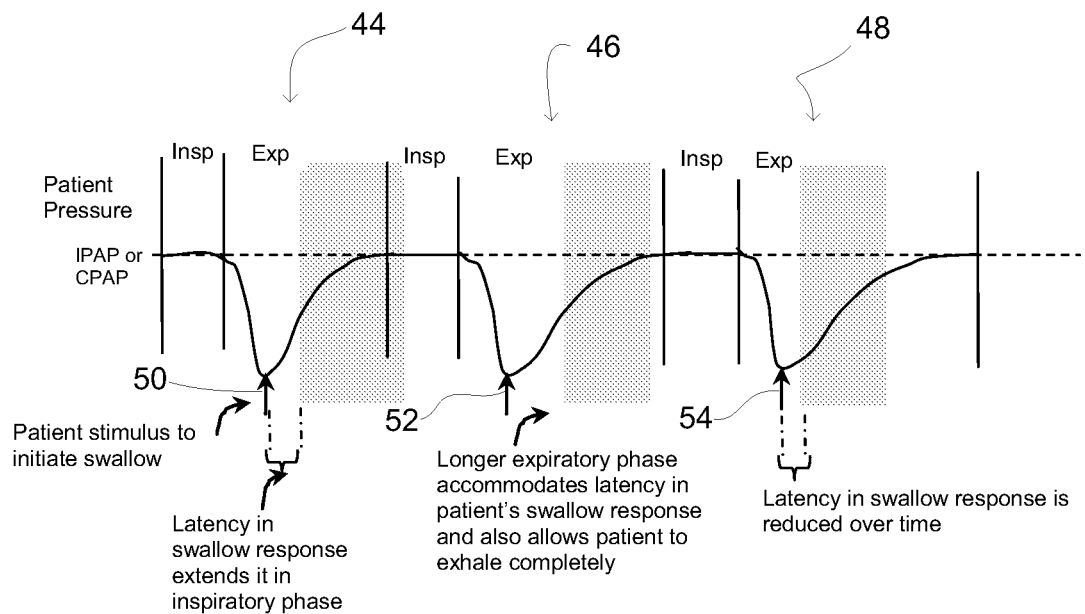
FIG. 5 illustrates a plot of pressure of a pressurized flow of breathable gas delivered to the airway of a subject versus time during therapy, according to one or more embodiments of the invention.

Returning to FIG. 1, in one embodiment, swallowing cue module 36 is configured to initiate swallowing cues at or near the middle of expiration by subject 12. By way of illustration, FIG. 5 is a plot of the pressure of the pressurized flow of breathable gas versus time. The pressure of the pressurized flow of breathable gas is provided as an indication of the respiratory cycle of the subject receiving therapy. As such, the principles discussed below with respect to FIG. 5 would still apply to an embodiment in which the pressurized flow of breathable gas is not generated and/or delivered to the subject. The plot of FIG. 5 shows three respiratory cycles 44, 46, and 48 in which swallowing cues are generated. It will be appreciated that the depiction of the three respiratory cycles being consecutive is illustrative. The three respiratory cycles depicted in FIG. 5 may actually occur consecutively, as shown, spaced apart in a single therapy session, and/or in separate therapy sessions.

In a first respiratory cycle 44, a swallowing cue is generated at a first point in time 50. In a second respiratory cycle 46, a swallowing cue is generated at a second point in time 52. In a third respiratory cycle 48, a swallowing cue is generated at a third point in time 54. The points in time 50, 52, and 54 may be determined and/or generation of the swallowing cues may be controlled by a swallowing cue module that is the same as or similar to swallowing cue module 36. As can be seen in FIG. 5, points in time 50, 52, and 54 are timed to coincide with a determined point in the expiration or respiratory cycles 44, 46, and 48 (e.g., at a point in time when patient pressure drops to a determined level).

The response of the subject to the swallowing cue generated at first point in time 50 has a period of latency. The dysphagia experienced by the subject tends to increase the latency of the subject's response to the swallowing cue. As can be seen in FIG. 5, this latency may cause the swallowing response to the swallowing cue to carry over into what would otherwise by inspiration.

In the second respiratory cycle 46, the parameters of the pressurized flow of breathable gas are adjusted to increase expiration time. Such an adjustment may be made, for example, by a generator control module that is the same as or similar to generator control module 34 (shown in FIG. 1). This increase in expiration time enables the subject to complete the swallow response to second point in time 52 before the inspiration period of second respiratory cycle 46.

The third respiratory cycle 48 illustrates improvements in swallowing ability made by the subject, over time, in response to therapy delivered to a subject by a system that is the same as or similar to system 10 (shown in FIG. 1). These improvements may include a reduction in the latency of the swallow response upon receiving the swallowing cue at third point in time 54.

Returning to FIG. 1, swallowing response module 38 is configured to determine a response of subject 12 to swallowing cues generated by system 10. This may include determining a beginning of a swallow, an end of a swallow, an amount of time required to perform a swallow, a latency of a swallowing response to the corresponding swallowing cue, and/or other information related to a swallow in response to a swallowing cue. The swallowing response module 38 determines the response of subject 12 to swallowing cues based on the output signals generated by swallowing sensors 22.

The performance evaluation module 40 is configured to evaluate the performance of subject 12 during therapy administered by system 10. This may include the performance of subject 12 with respect to a single swallowing cue, a set of swallowing cues, a single therapy session, and/or a set of therapy sessions. The evaluation performed by performance evaluation module 40 may include rating the ability of subject 12 to swallow based on determinations of swallowing response made by swallowing response module 38, rating the effectiveness of the therapy provided by system 10 over time, and/or other evaluations. One or more of the evaluations of performance evaluation module 40 may be presented to subject 12, a caregiver, a therapy decision maker, and/or other users via, for example, user interface 18.

The therapy module 42 is configured to set one or more parameters of a therapy regime administered to subject 12 by system 10. The one or more parameters may include, for example, one or more parameters of the pressurized flow of breathable gas delivered to subject 12, the timing of the points of time at which swallowing cues are administered with respect to respiratory cycle, the frequency of swallowing cues, the length of therapy sessions, and/or other parameters. At least one of the one or more parameters may be determined based on control inputs received, for example, from subject 12, from a caregiver, from a therapy decision maker, and/or from other users. At least one of the one or more parameters may be determined automatically by therapy module 42 based on evaluation of the performance of subject 12 by performance evaluation module 40.

Figure 6:
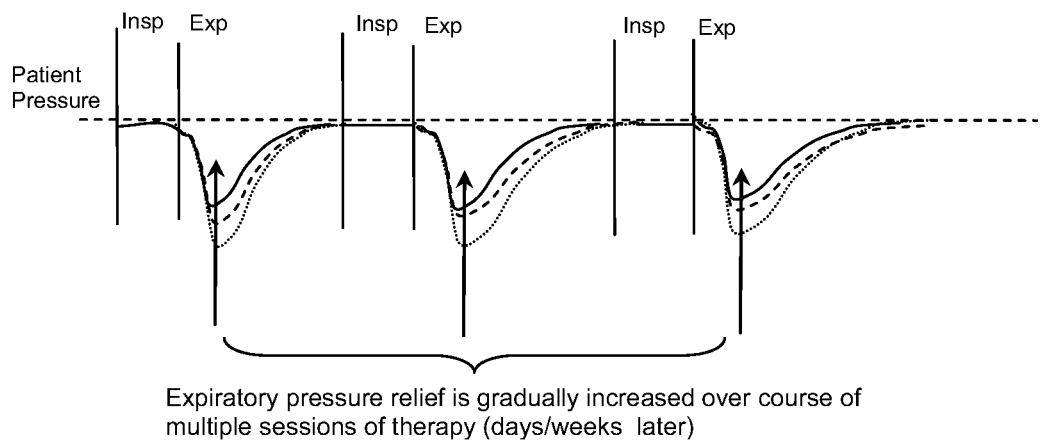
FIG. 6 illustrates a plot of pressure of a pressurized flow of breathable gas delivered to the airway of a subject versus time during therapy, according to one or more embodiments of the invention.

By way of illustration, FIG. 6 depicts one parameter adjustment that may be made over time. Specifically, FIG. 6 is a plot of time versus pressure of the pressurized flow of breathable gas that illustrates how this pressure may be reduced over time (e.g., from therapy session to therapy session, or within a single therapy session) as the swallowing function of the subject becomes stronger.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to treat dysphagia of a subject, the system comprising:
   a user interface configured to convey information to a subject;
   a swallowing sensor configured to generate an output signal indicating whether or not the subject is swallowing;
   a processor configured to execute computer program modules, the computer program modules comprising:
      a breathing parameter module configured to monitor a respiratory cycle of the subject and determine at least one of respiration rate, timing of breathing transitions between exhalation and inhalation, flow contour, and flow limitation;
      a swallowing cue module configured to control the user interface to provide swallowing cues to the subject that indicate the subject should attempt to swallow, the swallowing cue module further being configured to control the user interface to provide the swallowing cues to the subject at points in time in the respiratory cycle determined by the breathing cycle monitor;
      a swallowing response module configured to determine a response of the subject to the swallowing cues including determining a beginning of a swallow, an end of a swallow, an amount of time required to perform a swallow, a latency of a swallowing response to the corresponding swallowing cue in response to a swallowing cue, based on the output signals generated by swallowing sensors;
      a performance evaluation module configured to evaluate performance of the subject during administered therapy including performance of the subject with respect to at least one of a single swallowing cue, a set of swallowing cues, a single therapy session, and/or a set of therapy sessions to determine a rating of an ability of the subject to swallow based on the determinations of swallowing response made by the swallowing response module, and a rating the effectiveness of the therapy over time;
      a swallowing module configured to determine a response of the subject to a swallowing cue provided to the subject by the user interface, wherein the swallowing module determines the response of the subject based on the output signal of the sensor, the rating of the swallow ability and the rating of a therapy;
   a pressure generator configured to generate a pressurized flow of breathable gas for delivery to the airway of the subject concomitantly with the provision of swallowing cues to the subject by the user interface.

2. A system configured to treat dysphagia of a subject, the system comprising:
   a user interface configured to convey information to a subject;
   a subject interface device configured to communicate a pressurized flow of breathing gas to an airway of the subject, the subject interface device including a conduit and an interface appliance device, wherein the conduit conveys the pressurized flow of breathing gas to the subject interface device and the subject interface device includes at least one of a nasal cannula, a nasal mask, an oral mask, a full face mask, and a total face mask;

a sensor configured to generate an output signal indicating whether or not the subject is swallowing;

a processor configured to execute computer program modules, the computer program modules comprising:

a breathing parameter module configured to determine one or more breathing parameters of the breathing of the subject;

a swallowing cue module configured to control the user interface to provide swallowing cues to the subject that indicate the subject should attempt to swallow;

a performance evaluation module configured to evaluate a response of the subject to the swallowing cues provided to the subject by the user interface to determine at least one of a rating of the swallow responses and an effectiveness of a therapy over time based on a determination of the swallowing responses;

a swallowing module configured to determine a response of the subject to the swallowing cues provided to the subject by the user interface, wherein the evaluation includes at least one of rating a swallow ability and a rating of the effectiveness of the therapy made by the swallowing response over time, wherein the swallowing module determines the response of the subject based on the output signal of the sensor; and wherein the swallowing cue module is further configured to control the user interface to provide the swallowing cues to the subject at points in time determined based on the one or more breathing parameters determined by the breathing parameter module.

3. The system of claim 2, wherein the swallowing cue module is configured to initiate the swallowing cues adjacent a middle of expiration by the subject.

4. The system of claim 1, wherein the swallowing cue module is configured to initiate the swallowing cues adjacent a middle of expiration by the subject.

5. A method of treating dysphagia of a subject, the method comprising:

generating, with a swallowing sensor, an output signal indicating whether or not the subject is swallowing;

determining one or more breathing parameters of breathing of the subject;

providing a swallowing cue to the subject that indicates the subject should attempt to swallow, wherein providing the swallowing cue comprises providing the swallowing cue to the subject at a point in time determined based on the determined one or more breathing parameters;

determining a response of the subject to the swallowing cue including determining a beginning of a swallow, an end of a swallow, an amount of time required to perform a swallow, a latency of a swallowing response to the corresponding swallowing cue in response to a swallowing cue;

evaluating performance of the subject with respect to at least one of a single swallowing cue, a set of swallowing cues, a single therapy session, and/or a set of therapy sessions to determine a rating of an ability of the subject to swallow based on the determinations of swallowing response and a rating of effectiveness of the therapy over time; and generating a pressurized flow of breathable gas with a pressure generator device and delivering the pressurized flow of the breathing gas to an airway of the subject concomitantly with the provision of the swallowing cue to the subject.

6. The method of claim 5, further comprising initiating the swallowing adjacent a middle of expiration by the subject.

7. The method of claim 6, wherein the output signal conveys information related to breathing of the subject, and wherein determining the one or more breathing parameters comprises determining at least expiration and inhalation portions of a respiratory cycle of the subject.

8. The method of claim 5, further comprising evaluating the response of the subject to a plurality of swallowing cues.

9. A system configured to treat dysphagia of a subject, the system comprising:

an output signal generating means for generating an output signal indicating whether or not the subject is swallowing;

a breathing parameter determining means for determining one or more breathing parameters of the breathing of the subject;

a swallow cue providing means for providing a swallowing cue to the subject that indicates the subject should attempt to swallow at a point in time determined based on the determined one or more breathing parameters, the swallow cue providing means including at least one of an indicator light, a speaker, and a tactile feedback device;

a response determining means for determining a response of the subject to the swallowing cue provided to the subject based on the output signal of the sensor;

means for generating a pressurized flow of breathable gas to a subject interface for delivery to an airway of the subject concomitantly with the provision of the swallowing cue to the subject, the subject interface including a conduit and an appliance which conveys the pressurized flow of breathable gas to the airway.

10. The system of claim 9, wherein the response determining means determines a beginning of a swallow, an end of a swallow, an amount of time required to perform a swallow, a latency of a swallowing response to the corresponding swallowing cue in response to a swallowing cue, and further including:

a performance evaluation means for evaluating performance of the subject during administered therapy including performance of the subject with respect to at least one of a single swallowing cue, a set of swallowing cues, a single therapy session, and a set of therapy sessions to determine a rating of an ability of the subject to swallow based on the determinations of swallowing response made by the swallowing response means and a rating of effectiveness of the therapy over time.

11. The system of claim 9, wherein the swallowing cue providing means initiates the swallowing cue adjacent a middle of expiration portion of a respiratory cycle of the subject.

* * * * *